(12) United States Patent
Bergmann et al.

(10) Patent No.: US 9,702,876 B2
(45) Date of Patent: Jul. 11, 2017

(54) METHOD FOR PREDICTING THE RISK OF GETTING CANCER OR DIAGNOSING CANCER IN A FEMALE SUBJECT

(71) Applicant: SPHINGOTEC GMBH, Hennigsdorf (DE)

(72) Inventors: Andreas Bergmann, Berlin (DE); Olle Melander, Malmö (SE)

(73) Assignee: SPHINGOTEC GMBH, Hennigsdorf (DE)

( * ) Notice: Subject to any disclaimer, the term of this patent is extended or adjusted under 35 U.S.C. 154(b) by 0 days.

(21) Appl. No.: 14/432,808

(22) PCT Filed: Oct. 1, 2013

(86) PCT No.: PCT/EP2013/070471
§ 371 (c)(1),
(2) Date: Apr. 1, 2015

(87) PCT Pub. No.: WO2014/053502
PCT Pub. Date: Apr. 10, 2014

(65) Prior Publication Data
US 2015/0268240 A1 Sep. 24, 2015

(30) Foreign Application Priority Data
Oct. 2, 2012 (EP) .................................. 12187050

(51) Int. Cl.
*G01N 33/574* (2006.01)

(52) U.S. Cl.
CPC . *G01N 33/57415* (2013.01); *G01N 33/57423* (2013.01); *G01N 2333/665* (2013.01); *G01N 2800/50* (2013.01)

(58) Field of Classification Search
CPC ....... G01N 33/57415; G01N 33/57423; G01N 2333/665; G01N 2800/50
See application file for complete search history.

(56) References Cited

U.S. PATENT DOCUMENTS

| 8,013,123 B2 | 9/2011 | Bergmann et al. | |
| 2005/0181375 A1* | 8/2005 | Aziz | C12Q 1/6886 435/6.14 |
| 2008/0160557 A1 | 7/2008 | Cady | |
| 2008/0261232 A1 | 10/2008 | Bergmann et al. | |
| 2011/0294681 A1* | 12/2011 | Hinds | C12Q 1/6886 506/9 |
| 2011/0305633 A1* | 12/2011 | Forgez | C12Q 1/6886 424/1.69 |

FOREIGN PATENT DOCUMENTS

| AT | EP 2233590 A1 * | 9/2010 | ........... C12Q 1/6886 |
| EP | 2293079 A2 | 3/2011 | |

OTHER PUBLICATIONS

Ernst et al., Proenkephalin A 119-159, a stable pro-enkephalin A precursor fragment identified in human circulation, Peptides 27 (2006), 1835-1840.*
Anderson, The Clinical Plasma Proteome: A Survey of Clinical Assays for Proteins in Plasma and Serum, Clinical Chemistry, 56:2, 177-185 (2010).*
Ernst, Proneurotensin 1-117, a stable neurotensin precursor fragment identified in human circulation, Peptides 27 (2006) 1787-1793.*
Larsson et al., Diabetes mellitus and risk of breast cancer: a meta-analysis, Int. J. Cancer: 121, 856-862 (2007).*
Comb et al., CpG methylation inhibits proenkephalin gene expression and binding of the transcription factor AP-2, Nucleic Acids Research, vol. 18, No. 13, 1990 3975-3982.*
International Search Report dated Dec. 4, 2013 issued in corresponding PCT/EP2013/070471 application (pp. 1-5).
J.F. Dorgan et al., "Prospective Case-Control Study of Serum Mullerian Inhibiting Substance and Breast Cancer Risk", JNCI Journal of the National Cancer Institute, vol. 101, No. 21 (Oct. 2009) pp. 1501-1509.
Smith J. P. et al., "Methionine enkephalin: A new tumor marker for pancreatic cancer?", Pancreas, vol. 15, No. 4 (Nov. 1997) pp. 456.
Linnoila R. I. et al., "Decreased expression of neuropeptides in malignant paragangliomas: An immunohistochemical study", Human Pathology, vol. 19, No. 1 (Jan. 1988) pp. 41-50.

* cited by examiner

*Primary Examiner* — Andrea S Grossman
(74) *Attorney, Agent, or Firm* — Millen, White, Zelano, Branigan, P.C.

(57) ABSTRACT

Subject matter of the present invention is a method for predicting the risk of getting cancer in a female subject that does not suffer from cancer or alternatively diagnosing cancer in a female subject comprising:
determining the level of Pro-Enkephalin or fragments thereof including Leu-Enkephalin and Met-Enkephalin of at least 5 amino acids in a bodily fluid obtained from said female subject; and
correlating said level of Pro-Enkephalin or fragments thereof with a risk for getting cancer, wherein a reduced level is predictive for an enhanced risk of getting cancer or alternatively diagnosing cancer wherein an reduced level is correlated with the diagnosis of cancer.

20 Claims, 4 Drawing Sheets

Figure 1:
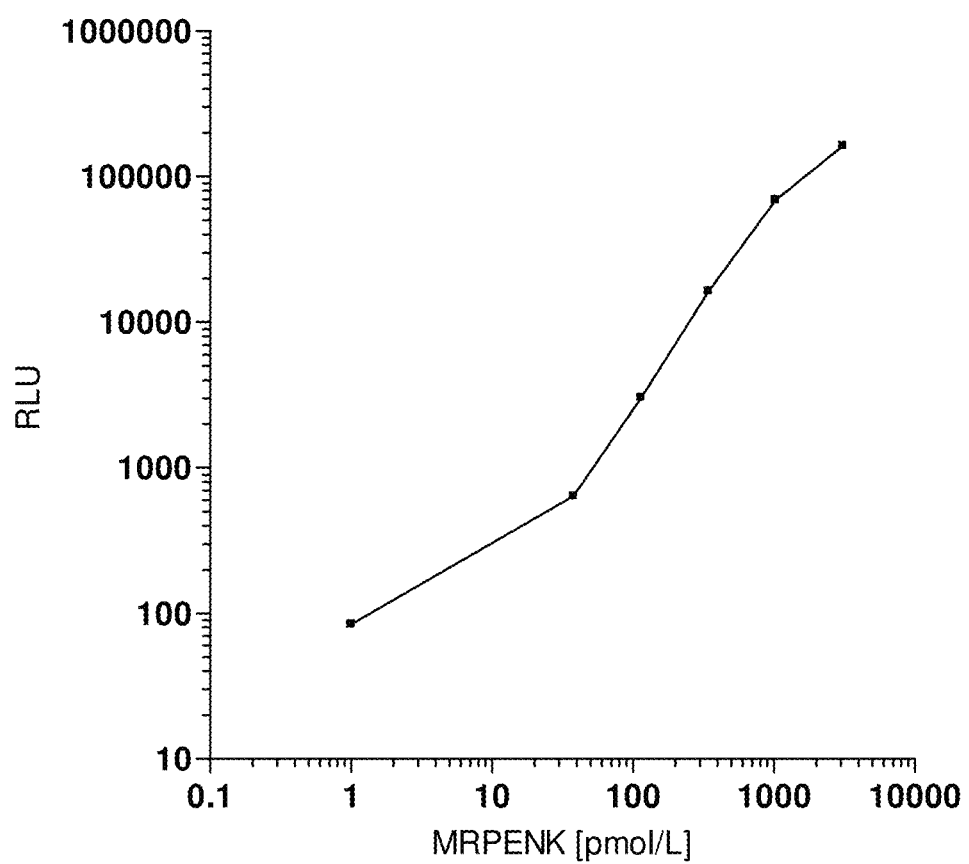

METHOD FOR PREDICTING THE RISK OF GETTING CANCER OR DIAGNOSING CANCER IN A FEMALE SUBJECT

Subject matter of the present invention is a method for predicting the risk of getting cancer in a female subject that does not suffer from cancer or alternatively diagnosing cancer in a female subject comprising:
- determining the level of Pro-Enkephalin (PENK) or fragments thereof including Leu-Enkephalin and Met-Enkephalin of at least 5 amino acids in a bodily fluid obtained from said female subject; and
- correlating said level of Pro-Enkephalin or fragments thereof with a risk for getting cancer, wherein a reduced level is predictive for an enhanced risk of getting cancer or alternatively diagnosing cancer wherein an reduced level is correlated with the diagnosis of cancer.

Met-Enkephalin, a 5 amino acid peptide derived from the Enkephalin precursor (PreProEnkephalin), also named "Opioid Growth Factor" (OGF) is released together with ProEnkephalin-fragments. The mature peptide binds to different opioid receptors (Koneru et al., 2009). Enkephalin (OGF) was found to have a number of physiological functions. In the CNS it down regulates Substance P associated pain signalling, it plays roles as cytokine (Plotnikoff et al., 1997). Proenkephalin related peptides exhibiting antibiotic actions (Goumon et al., 1998). Proenkephalin and Enkephalin exhibits anti tumor action and acting as pro-apoptotic agents (Tavish et al., 2007, Donahue et al., 2011, Zagon et al., 2009).

The use of vasoactive peptides for prediction of cancer risks in males has been reported by Belting et al., Cancer, Epidemiology, Biomarkes & Prevention. MR-pro-ANP, MR-pro-ADM and copeptin was measured in the fasting plasma from participants of the Malmö Diet and Cancer Study that were free from cancer prior to the baseline exam in 1991 to 1994 (1768 males and 2293 females). The authors stated that among females, there was no relationship between biomarkers and cancer incidence.

A subject of the present invention was to investigate the prognostic and diagnostic power of PENK for the prediction of cancer incidence and the prediction of the risk of reoccurrence of cancer. To address this issue, stable fragments of Pro-Enkephalin (Ernst et al., 2006) in fasting plasma were measured in said Swedish prospective cohort study (Malmö Diet and Cancer Study) and related baseline level of this biomarker to breast-cancer incidence during 15 years of follow-up.

Surprisingly, it has been shown that Pro-Enkephalin is a powerful and highly significant biomarker for woman for predicting the risk of getting cancer in a female subject that does not suffer from cancer or alternatively diagnosing cancer in a female subject.

Thus, subject matter of the present invention is a method for predicting the risk of getting cancer in a female subject that does not suffer from cancer or alternatively diagnosing cancer in a female subject comprising:
- determining the level of Pro-Enkephalin or fragments thereof of at least 5 amino acids in a bodily fluid obtained from said female subject; and
- correlating said level of Pro-Enkephalin or fragments thereof with a risk for getting cancer, wherein an reduced level is predictive for an enhanced risk of getting cancer or alternatively diagnosing cancer wherein an reduced level is correlated with the diagnosis of cancer.

Examples of cancers may be selected from the group comprising breast cancer, lung cancer, pancreatic cancer and colon cancer.

Throughout the specification it should be understood that the term fragments of Pro-Enkephalin also include Leu-Enkephalin and Met-Enkephalin.

In a specific embodiment of the invention said cancer is breast cancer. In another specific embodiment of the invention said cancer is lung cancer.

Thus, subject matter of the present invention is the determination of susceptibility of a woman to acquire cancer, e.g. breast cancer, lung cancer etc.

Data obtained in the present study revealed also a correlation between the risk of getting cancer in male subjects with the level of Pro-Enkephalin or fragments thereof of at least 5 amino acids in a bodily fluid obtained from said male subject; this correlation however, was not that statistically significant for the present data set although there was a clear trend for an increased cancer risk at reduced levels of PENK also in males. Thus, there is a value for the method according to the invention also for male subjects but in the present study the observed effect was not as strong for males as compared to females. This may be primarily due to the low number of cancer incidents in the male population.

Further, data obtained in the present study revealed also a correlation between the risk of getting cancer in female subjects with the level of Pro-Enkephalin or fragments thereof of at least 5 amino acids in a bodily fluid obtained from said female subject, wherein said cancer was not lung cancer or breast cancer. Due to the small number of incidents in this particular population this correlation however, was not that statistically significant for the present data set. Although it was not significant there was a clear trend. It is furthermore credible that the present data suggest such a correlation also in other cancers due to the known proapoptotic effect of Enkephalin, a fragment of PENK. Starting from the prior art it is surprising that Pro-Enkephalin or fragments thereof may be predictive for cancer. Starting from the present data that are statistically highly relevant for breast cancer and lung cancer it is to be expected and credible that it may be prognostic for other types of cancer as well.

The term "subject" as used herein refers to a living human or non-human organism. Preferably herein the subject is a human subject.

The term "reduced level" means a level below a certain threshold level.

A bodily fluid may be selected from the group comprising blood, serum, plasma, urine, cerebro spinal liquid (csf), and saliva.

In one embodiment of the invention said female subject has never had a diagnosed cancer at the time the sample of bodily fluid is taken from said female subject.

In another embodiment said female subject has been diagnosed before with having cancer and has been cured at the time the sample of bodily fluid is taken from said female subject and the risk of reoccurrence of getting cancer is determined or alternatively the re-occurrence of cancer is predicted.

Pro-Enkephalin has the following sequence:

```
(Pro-Enkphalin (1-243)
                                          SEQ ID NO. 1
ECSQDCATCSYRLVRPADINFLACVMECEGKLPSLKIWETCKELLQLSK

PELPQDGTSTLRENSKPEESHLLAKRYGGFMKRYGGFMKKMDELYPMEP
```

-continued

```
EEEANGSEILAKRYGGFMKKDAEEDDSLANSSDLLKELLETGDNRERSH

HQDGSDNEEEVSKRYGGFMRGLKRSPQLEDEAKELQKRYGGFMRRVGRP

EWWMDYQKRYGGFLKRFAEALPSDEEGESYSKEVPEMEKRYGGFMRF
```

Fragments of Pro-Enkephalin that may be determined in a bodily fluid may be e.g. selected from the group of the following fragments:

```
(Synenkephalin, Pro-Enkephalin 1-73)
                                    SEQ ID NO. 2
ECSQDCATCSYRLVRPADINFLACVMECEGKLPSLKIVVETCKELLQLS

KPELPQDGTSTLRENSKPEESHLLA (Met-Enkephalin)
                                    SEQ ID NO. 3
YGGFM (Leu-Enkephalin)
                                    SEQ ID NO. 4
YGGFL (ProEnkephalin 90-109)
                                    SEQ ID NO. 5
MDELYPMEPEEEANGSEILA SEQ ID NO. 6
(Pro Enkephalin 119-159, Mid regional
Pro-Enkephalin-fragment, MRPENK)
DAEEDDSLANSSDLLKELLETGDNRERSHHQDGSDNEEEVS SEQ ID NO. 7
(Met-Enkephalin-Arg-Gly-Leu)
YGGFMRGL SEQ ID NO. 8
(Pro-Enkephalin 172-183)
SPQLEDEAKELQ SEQ ID NO. 9
(Pro-Enkephalin 193-203)
VGRPEWWMDYQ SEQ ID NO. 10
(Pro-Enkephalin 213-234)
FAEALPSDEEGESYSKEVPEME SEQ ID NO. 11
(Pro-Enkephalin 213-241)
FAEALPSDEEGESYSKEVPEMEKRYGGF M SEQ ID NO. 12
(Met-Enkephalin-Arg-Phe)
YGGFMRF
```

SEQ ID NO. 26 (ProEnkephalin 119-125 with N-terminal cysteine) (C)DAEEDD
SEQ ID NO. 27 (ProEnkephalin 121-134 with N-terminal cysteine) (C)EEDDSLANSSDLLK
SEQ ID NO. 28 (ProEnkephalin 133-140 with N-terminal cysteine) (C)LKELLETG
SEQ ID NO. 29 (ProEnkephalin 139-155 with N-terminal cysteine) (C)TGDNRERSHHQDGSDNE
SEQ ID NO. 30 (ProEnkephalin 152-159 with N-terminal cysteine) (C)SDNEEEVS Determining the level of Pro-Enkephalin including Leu-Enkephalin and Met-Enkephalin or fragments thereof may mean that the immunoreactivity towards Pro-Enkephalin or fragments thereof including Leu-Enkephalin and Met-Enkephalin is determined. A binder used for determination of Pro-Enkephalin including Leu-Enkephalin and Met-Enkephalin or fragments thereof depending of the region of binding may bind to more than one of the above displayed molecules. This is clear to a person skilled in the art.

Thus, according to the present invention the level of immunoreactive analyte by using at least one binder that binds to a region within the amino acid sequence of any of the above peptide and peptide fragments, (i.e. Pro-Enkephalin (PENK) and fragments according to any of the sequences 1 to 12), is determined in a bodily fluid obtained from said subject; and correlated to the specific embodiments of clinical relevance.

In a more specific embodiment of the method according to the present invention the level of MRPENK is determined (SEQ ID NO. 6: Pro-Enkephalin 119-159, Mid regional Pro-Enkephalin-fragment, MRPENK). In a more specific embodiment the level of immunoreactive analyte by using at least one binder that binds to MR-PENK is determined and is correlated to the specific embodiments of clinical relevance according to the invention.

Determining the level of Pro-Enkephalin or fragments thereof including Leu-Enkephalin and Met-Enkephalin or fragments thereof may mean that the immunoreactivity towards Pro-Enkephalin or fragments thereof including Leu-Enkephalin and Met-Enkephalin is determined. A binder used for determination of Pro-Enkephalin including Leu-Enkephalin and Met-Enkephalin or fragments thereof depending of the region of binding may bind to more than one of the above displayed molecules. This is clear to a person skilled in the art. In another embodiment of the invention the fragment is not Leu-Enkephalin or Met-Enkephalin, In another embodiment of the invention the immunoreactivity towards Pro-Enkephalin or fragments thereof not including Leu-Enkephalin and Met-Enkephalin is determined.

In a more specific embodiment of the method according to the present invention the level of MRPENK. (SEQ ID NO. 6 (Pro Enkephalin 119-159, Mid regional Pro-Enkephalin-fragment, MRPENK, DAEEDDSLANSSDLLKEL-LETGDNRERSHHQDGSDNEEEVS) is determined.

Alternatively the level of any of the above analytes may be determined by other analytical methods e.g. mass spectroscopy.

In a specific embodiment the level of Pro-Enkephalin or fragments thereof are measured with an immunoassay using antibodies or fragments of antibodies binding to Pro-Enkephalin or fragments thereof. An immunoassay that may be useful for determining the level of Pro-Enkephalin or fragments thereof of at least 5 amino acids may comprise the steps as outlined in Example 2. All thresholds and values have to be seen in correlation to the test and the calibration used according to Example 2. A person skilled in the art may know that the absolute value of a threshold might be influenced by the calibration used. This means that all values and thresholds given herein are to be understood in context of the calibration used in herein (Example 2). According to the invention the diagnostic binder to Pro-Enkephalin is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines.

In a specific embodiment the level of Pro-Enkephalin or fragments thereof are measured with an assay using binders selected from the group comprising aptamers, non-Ig scaffolds as described in greater detail below binding to Pro-Enkephalin or fragments thereof.

Binder that may be used for determining the level of Pro-Enkephalin or fragments thereof exhibit an affinity constant to Pro-Enkephalin of at least $10^7$ $M^{-1}$, preferred $10^8$ $M^{-1}$, preferred affinity constant is greater than $10^9$ $M^{-1}$, most preferred greater than $10^{10}$ $M^{-1}$. A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany.

A human Pro-Enkephalin-control sample is available by ICI-Diagnostics, Berlin, Germany. The assay may also be calibrated by synthetic (for our experiments we used synthetic MRPENK, SEQ ID NO. 6) or recombinant Pro-Enkephalin or fragments thereof.

The threshold for determining the risk of getting breast cancer in a female subject or diagnosing breast cancer in a female subject according to the methods of the present invention is below 100 pmol/l PENK, preferred below 50 pmol/l, more preferred below 40.4 pmol/l. In a specific embodiment said threshold is about 40.4 pmol/l. These thresholds are related to the above mentioned calibration method. A PENK value below said threshold means that the subject has an enhanced risk of getting cancer or has already cancer.

In one embodiment of the invention said method is performed more than once in order to monitor the risk of getting breast cancer in a female subject or in order to monitor the course of treatment. In one specific embodiment said monitoring is performed in order to evaluate the response of said female subject to preventive and/or therapeutic measures taken.

In one embodiment of the invention the method is used in order to stratify said female subjects into risk groups.

Subject of the present invention is also a method for predicting the risk of getting cancer in a female or identifying a female subject having an enhanced risk for getting cancer according to any of the preceding embodiments, wherein the level of Pro-Enkephalin or fragments thereof of at least 5 amino acids in a bodily fluid obtained from said female subject either alone or in conjunction with other prognostically useful laboratory or clinical parameters is used for the prediction of a subject's risk for getting an adverse event by a method which may be selected from the following alternatives:

Comparison with the median of the level of Pro-Enkephalin or fragments thereof of at least 5 amino acids in a bodily fluid obtained from said female subject in an ensemble of pre-determined samples in a population of "healthy" or "apparently healthy" subjects, Comparison with a quantile of the level of Pro-Enkephalin or fragments thereof of at least 5 amino acids in a bodily fluid obtained from said female subject in an ensemble of pre-determined samples in a population of "healthy" or "apparently healthy" subjects, Calculation based on Cox Proportional Hazards analysis or by using Risk index calculations such as the NRI (Net Reclassification Index) or the IDI (Integrated Discrimination Index).

In one embodiment of the invention subject of the present invention is also a method for predicting the risk of getting cancer in a female or identifying a female subject having an enhanced risk for getting cancer according to any of the preceding embodiments, wherein the level of Pro-Enkephalin or fragments thereof of at least 5 amino acids in a bodily fluid obtained from said female subject either alone or in conjunction with other prognostically useful biomarker. Such a useful biomarker may be Pro-Neurotensin and fragments thereof of at least 5 amino acids.

In a more specific embodiment of the method according to the present invention the level of Pro-Neurotensin 1-117 is determined in addition to the determination of Pro-Enkephalin an fragments thereof.

Thus, subject matter of the present invention is also a method for predicting the risk of getting cancer in a female subject that does not suffer from cancer or alternatively diagnosing cancer in a female subject comprising:

determining the level of Pro-Enkephalin or fragments thereof including Leu-Enkephalin and Met-Enkephalin of at least 5 amino acids in a bodily fluid obtained from said female subject; and determining the level of Pro-Neurotensin or fragments thereof of at least 5 amino acids in a bodily fluid obtained from said female subject; and correlating said level of Pro-Enkephalin or fragments thereof and Pro-Neurotensin or fragments thereof of at least 5 amino acids with a risk for getting cancer, wherein an reduced level of Pro-Enkephalin is predictive for an enhanced risk of getting cancer or alternatively diagnosing cancer wherein an reduced level is correlated with the diagnosis of cancer and wherein an increased level of Pro-Neurotensin is predictive for an enhanced risk of getting cancer or alternatively diagnosing cancer wherein an increased level is correlated with the diagnosis of cancer.

```
(Pro-Neurotensin 1-147)
                                          SEQ ID NO. 13
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY ENKPRRPYIL KRDSYYY (Pro-Neurotensin 1-125 (large neuromedin N))
                                          SEQ ID NO. 14
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVI KR

KIPYIL (neuromedin N)
                                          SEQ ID NO. 15
KIPYIL (neurotensin)
                                          SEQ ID NO. 16
pyroQLYENKPRRP YIL
```

```
(Pro-Neurotensin 1-117)
                                         SEQ ID NO. 17
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVI (Pro-Neurotensin 1-132)
                                         SEQ ID NO. 18
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY EN (Pro-Neurotensin 120-140)
                                         SEQ ID NO. 19
KIPYILKRQL YENKPRRPYI L (Pro-Neurotensin 120-147)
                                         SEQ ID NO. 20
KIPYILKRQL YENKPRRPYIL KRDSYYY (Pro-Neurotensin 128-147)
                                         SEQ ID NO. 21
QLYENKPRRP YILKRDSYYY
```

In a specific embodiment the level of Pro-Neurotensin is measured with an immunoassay. More specifically an immunoassay is used as described in Ernst et al. (Peptides (2006), (27) 1787-1793). An immunoassay that may be useful for determining the level of Pro-Neurotensin or fragments thereof of at least 5 amino acids may comprise the steps as outlined in Example 2. All thresholds and values have to be seen in correlation to the test and the calibration used according to Example 2. A person skilled in the art may know that the absolute value of a threshold might be influenced by the calibration used. This means that all values and thresholds given herein are to be understood in context of the calibration used in herein (Example 2). A human Pro-Neurotensin-calibrator is available by ICI-Diagnostics, Berlin, Germany. Alternatively, the assay may also be calibrated by synthetic or recombinant P-NT 1-117 or fragments thereof (see also Ernst et al, 2006).

Binder that may be used for determining the level of Pro-Neurotensin or fragments thereof exhibit an affinity constant to Pro-Neurotensin of at least $10^7$ M$^{-1}$, preferred $10^8$ M$^{-1}$, preferred affinity constant is greater than $10^9$ M$^{-1}$, most preferred greater than $10^{10}$ M$^{-1}$. A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany. The threshold for determining the risk of getting breast cancer in a female subject or diagnosing breast cancer in a female subject according to the methods of the present invention is above 78 pmol/l PNT, preferred 100 pmol/l, more preferred 150 pmol/l. In a specific embodiment said threshold is about 100 pmol/l. These thresholds are related to the above mentioned calibration method. A P-NT value above said threshold means that the subject has an enhanced risk of getting cancer or has already cancer.

In one embodiment of the invention said method is performed more than once in order to monitor the risk of getting breast cancer in a female subject or in order to monitor the course of treatment. In one specific embodiment said monitoring is performed in order to evaluate the response of said female subject to preventive and/or therapeutic measures taken.

In one embodiment of the invention the method is used in order to stratify said female subjects into risk groups.

In one embodiment of the invention the cancer is selected from the group comprising breast cancer, and lung cancer.

Subject matter of the invention is further an assay for determining Pro-Enkephalin and Pro-Enkephalin fragments in a sample comprising two binders that bind to two different regions within the region of Pro-Enkephalin that is amino acid 133-140 (LKELLETG, SEQ ID NO. 22) and amino acid 152-159 (SDNEEEVS, SEQ ID NO. 23) wherein each of said regions comprises at least 4 or 5 amino acids.

In one embodiment of the assays for determining Pro-Enkephalin or Pro-Enkephalin fragments in a sample according to the present invention the assay sensitivity of said assay is able to quantify the Pro-Enkephalin or Pro-Enkephalin fragments of healthy subjects and is <15 pmol/L, preferably <10 pmol/L and more preferably <6 pmol/L.

In one embodiment of the assays for determining Pro-Enkephalin or Pro-Enkephalin fragments in a sample according to the present invention said binder exhibits an binding affinity to its binding partner of at least $10^7$ M$^{-1}$, preferred $10^8$ M$^{-1}$, preferred affinity constant is lower than $10^9$ M$^{-1}$, most preferred lower than $10^{10}$ M$^{-1}$. A person skilled $_{[K1]}$ in the art knows that it may be considered to compensate lower affinity by applying a higher dose of compounds and this measure would not lead out-of-the-scope of the invention binding affinity may be determined as described above.

In one embodiment of the assays for determining Pro-Enkephalin or Pro-Enkephalin fragments in a sample according to the present invention such assay is a sandwich assay, preferably a fully automated assay. It may be an ELISA fully automated or manual. It may be a so-called POC-test (point-of-care). Examples of automated or fully automated assay comprise assays that may be used for one of the following systems: Roche ELECSYS®, Abbott ARCHITECT®, Siemens CENTAUER®, Brahms KRYPTOR®, Biomerieux VIDAS®, and Alere TRIAGE®. Examples of test formats are provided above.

In one embodiment of the assays for determining Pro-Enkephalin or Pro-Enkephalin fragments in a sample according to the present invention at least one of said two binders is labeled in order to be detected. Examples of labels are provided above.

In one embodiment of the assays for determining Pro-Enkephalin or Pro-Enkephalin fragments in a sample according to the present invention at least one of said two binders is bound to a solid phase. Examples of solid phases are provided above.

In one embodiment of the assays for determining Pro-Enkephalin or Pro-Enkephalin fragments in a sample according to the present invention said label is selected from the group comprising chemiluminescent label, enzyme label, fluorescence label, radioiodine label.

A further subject of the present invention is a kit comprising an assay according to the present invention wherein the components of said assay may be comprised in one or more container.

EXAMPLES

Example 1

Development of Antibodies

Peptides

Peptides were synthesized (JPT Technologies, Berlin, Germany).

Peptides/Conjugates for Immunization:

Peptides for immunization were synthesized (JPT Technologies, Berlin, Germany) with an additional N-terminal Cystein residue for conjugation of the peptides to bovine serum albumin (BSA). The peptides were covalently linked to BSA by using Sulfo-SMCC (Perbio-science, Bonn, Germany). The coupling procedure was performed according to the manual of Perbio.

TABLE 1

| Peptide for immunization | Pro-Enkephalin sequence |
|---|---|
| (C)DAEEDD (SEQ ID NO: 26) | 119-125 |
| (C)EEDDSLANSSDLLK (SEQ ID NO: 27) | 121-134 |
| (C)LKELLETG (SEQ ID NO: 28) | 133-140 |
| (C)TGDNRERSHHQDGSDNE (SEQ ID NO: 29) | 139-155 |
| (C)SDNEEEVS (SEQ ID NO: 30) | 152-159 |

The antibodies were generated according to the following method:

A BALB/c mouse was immunized with 100 µg peptide-BSA-conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitonal and one intravenous injection.

Spenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Monoclonal Antibody Production

Antibodies were produced via standard antibody production methods (Marx et al., Monoclonal Antibody Production (1997), ATLA 25, 121) and purified via Protein A-chromatography. The antibody purities were >95% based on SDS gel electrophoresis analysis.

Labelling and Coating of Antibodies.

All antibodies were labelled with acridinium ester according the following procedure:

Labelled compound (tracer): 100 µg (100 µl) antibody (1 mg/ml in PBS, pH 7.4, was mixed with 10 µl Acridinium NHS-ester (1 mg/ml in acetonitrile, InVent GmbH, Germany) (EP 0353971) and incubated for 20 min at room temperature. Labelled antibody was purified by gel-filtration HPLC on Bio-Sil SEC 400-5 (Bio-Rad Laboratories, Inc., USA) The purified labelled antibody was diluted in (300 mmol/l potassiumphosphate, 100 mmol/l NaCl, 10 mmol/l Na-EDTA, 5 g/l bovine serum albumin, pH 7.0). The final concentration was approx. 800.000 relative light units (RLU) of labelled compound (approx. 20 ng labeled antibody) per 200 µl. Acridiniumester chemiluminescence was measured by using an AutoLumat LB 953 (Berthold Technologies GmbH & Co. KG).

Solid Phase Antibody (Coated Antibody):

Solid phase: Polystyrene tubes (Greiner Bio-One International AG, Austria) were coated (18 h at room temperature) with antibody (1.5 µg antibody/0.3 ml 100 mmol/l NaCl, 50 mmol/l Tris/HCl, pH 7.8). After blocking with 5% bovine serum albumine, the tubes were washed with PBS, pH 7.4 and vacuum dried.

Antibody Specificity:

The crossreactivities of the different antibodies are listed in table 2.

TABLE 2

| Peptide for immunization | Pre-Pro-Enkephalin-sequence | Antibody name |
|---|---|---|
| (C)DAEEDD (SEQ ID NO: 26) | 119-125 | NT-MRPENK |
| (C)EEDDSLANSSDLLK (SEQ ID NO: 27) | 121-134 | NM-MRPENK |
| (C)LKELLETG (SEQ ID NO: 28) | 133-140 | MR-MRPENK |
| (C)TGDNRERSHHQDGSDNE (SEQ ID NO: 29) | 139-155 | MC-MRPENK |
| (C)SDNEEEVS (SEQ ID NO: 30) | 152-159 | CT-MRPENK |

Antibody cross-reactivities were determined as follows:

1 ug peptide in 300 µl PBS, pH 7.4 was pipetted into Polystyrene tubes and incubated for 1 h at room temperature. After incubation the tubes were washed 5 times (each 1 ml) using 5% BSA in PBS, pH 7.4. Each of the labelled antibodies were added (300 µl in PBS, pH 7.4, 800.000 RLU/300 µl) an incubated for 2 h at room temperature, After washing 5 times (each 1 ml of washing solution (20 mmol/l PBS, pH 7.4, 0.1% Triton X 100), the remaining luminescence (labelled antibody) was quantified using the AutoLumat LB 953. MRPENK-peptide (SEQ ID NO: 6) was used as reference substance (100%).

TABLE 3

| peptide | antibody | | | | | |
|---|---|---|---|---|---|---|
| | DAEEDD (SEQ ID NO: 26) | EEDDSLANSSD LLK (SEQ ID NO: 27) | LKELLETG (SEQ ID NO: 28) | TGDNRERSH HQDGSDNE (SEQ ID NO: 29) | SDNEEEVS (SEQ ID NO: 30) | MRPENK (SEQ ID NO. 6) |
| NT-MRPENK | 121 | 10 | <1 | <1 | <1 | 100 |
| NM-MRPENK | <1 | 98 | <1 | <1 | <1 | 100 |
| MR-MRPENK | <1 | <1 | 105 | <1 | <1 | 100 |
| MC-MRPENK | <1 | <1 | <1 | 115 | <1 | 100 |
| CT-MRPENK | <1 | <1 | <1 | <1 | 95 | 100 |

All antibodies bound the MRPENK peptide (SEQ ID NO. 6), comparable to the peptides which were used for immunization. Except for NT-MRPENK-antibody (10% cross reaction with EEDDSLANSSDLLK) (SEQ ID NO. 27) no antibody showed a cross reaction with MR-PENK peptides not used for immunization of the antibody.

Pro-Enkephalin Immunoassay:

50 μl of sample (or calibrator) was pipetted into coated tubes, after adding labeled antibody (200 μl), the tubes were incubated for 2 h at 18-25° C. Unbound tracer was removed by washing 5 times (each 1 ml) with washing solution (20 mmol/l PBS, pH 7.4, 0.1% Triton X-100). Tube-bound labelled antibody was measured by using the Luminumeter LB 953 and a fixed concentration of 1000 pmol/l of MRPENK. The signal (RLU at 1000 pmol MRPENK/l) to noise (RLU without MRPENK) ratio of different antibody combinations is given in table 4. All antibodies were able to generate a sandwich complex with any other antibody. Surprisingly, the strongest signal to noise ratio (best sensitivity) was generated by combining the MR-MRPENK- and CT-MRPENK antibody. Subsequently, we used this antibody combination to perform the MRPENK-immunoassay for further investigations. MR-MRPENK antibody was used as coated tube antibody and CT-MRPENK antibody was used as labelled antibody.

TABLE 4

| Labelled antibody | Solid phase antibody | | | | |
|---|---|---|---|---|---|
| | NT-MRPENK | NM-MRPENK | MR-MRPENK | MC-MRPENK | CT-MRPENK |
| NT-MRPENK | / | 27 | 212 | 232 | <1 |
| NM-MRPENK | 36 | / | 451 | 487 | <1 |
| MR-MRPENK | 175 | 306 | / | 536 | 1050 |
| MC-MRPENK | 329 | 577 | 542 | / | <1 |
| CT-MRPENK | <1 | 615 | 1117 | 516 | / |

Calibration:

The assay was calibrated, using dilutions of synthetic MRPENK (SEQ ID NO. 6), diluted in 20 mM K2PO4, 6 mM EDTA, 0.5% BSA, 50 μM Amastatin, 100 μM Leupeptin, pH 8.0. Pro-Enkephalin control plasma is available at ICI-diagnostics, Berlin, Germany.

FIG. 1 shows a typical Pro-Enkephalin dose/signal curve. Standard curve Pro-Enkephalin.

The assay sensitivity was 20 determinations of 0-calibrator (no addition of MRPENK)+2SD) 5.5 pmol/L.

Population Study

Methods

We measured Pro-Enkephalin in fasting plasma from 2559 female participants of the population based Malmö Diet and Cancer Study baseline exam in 1991-1994 (age 58±6 years and 59% females). We used multivariable adjusted (all traditional cardiovascular risk factors, diabetes risk factors and in analyses of cancer also heredity for cancer) Cox proportional hazards models to relate baseline PENK (hazard ratio per each standard deviation increase of log-transformed PENK) to the time to the first event of each of the studied endpoints during a median follow-up time of more than 12 years. Endpoints were retrieved through the Swedish National Hospital Discharge Registry, the Swedish Myocardial Infarction Registry, the Stroke in Malmö Registry and the Swedish Cancer Registry. Retrieval of endpoints through these registries has been validated and found to be accurate (see also Belting et al. Cancer Epidemiol Biomarkers Prev; 1-10. 2012 AACR).

Clinical Characteristics of Females in the Study

TABLE 5

| Descriptive Statistics | | | |
|---|---|---|---|
| | N | Mean | Std. Deviation |
| Age at MDCS screening | 2559 | 57.554 | 5.9403 |
| Systolic blood pressure (mmHg) | 2559 | 140.50 | 19.311 |
| Diastolic blood pressure (mmHg) | 2559 | 85.65 | 9.117 |
| body-mass-index (weight/kg x kg) | 2559 | 25.5196 | 4.19083 |
| WAIST (cm) | 2559 | 76.99 | 10.245 |
| Glucose (mmol/l) | 2559 | 5.0418 | 1.21798 |
| Triglycerides (mmol/l) | 2559 | 1.2245 | .58404 |
| High density lipoprotein (mmol/l) | 2559 | 1.5123 | .36949 |
| Low density lipoprotein (mmol/l) | 2559 | 4.2016 | 1.04762 |
| P-INSULIN | 2512 | 7.223 | 5.4223 |

Figure 2:
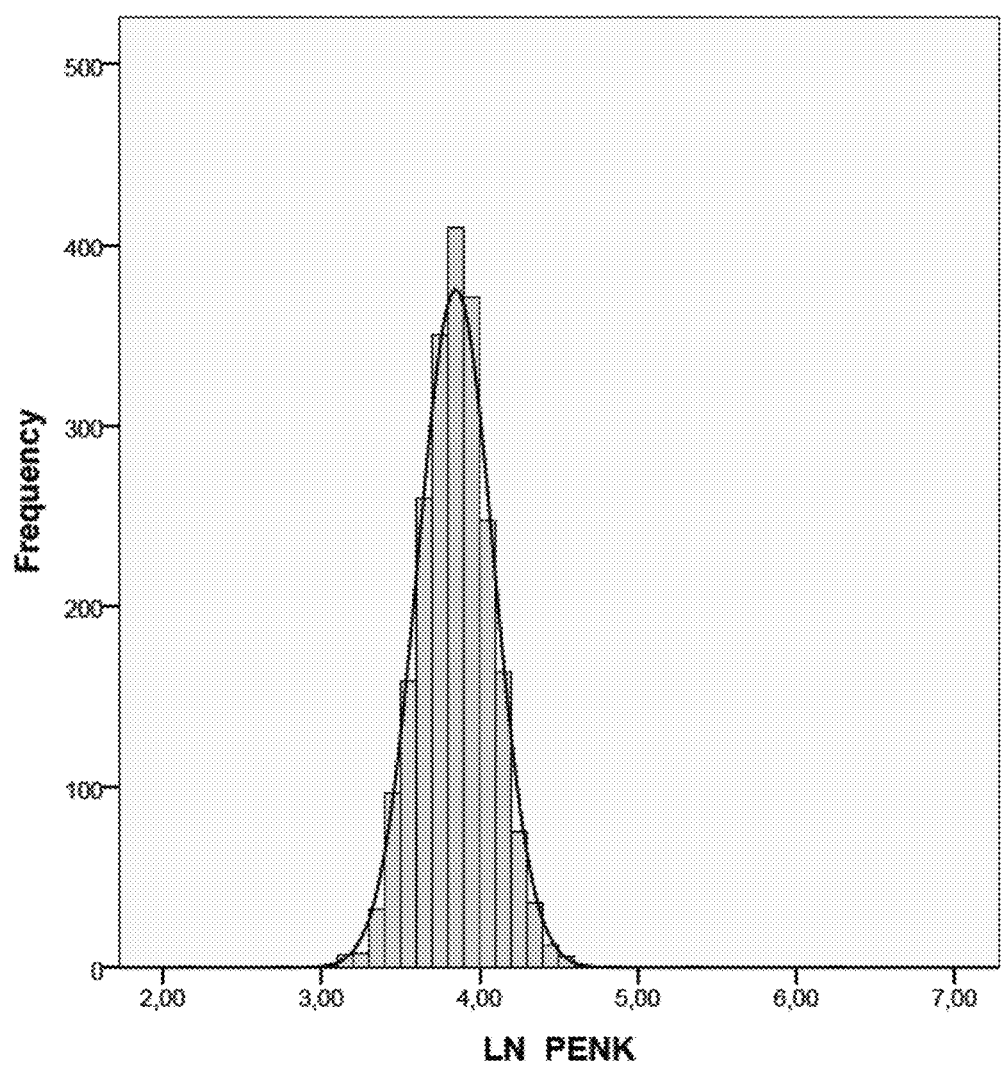

FIG. 2: frequency distribution of Pro Enkephalin in the females population:

The mean value was 47.2 pmol/L, standard deviation=1.2 pmol/L. The x axis is the Logarithmus Naturalis (LN) of the PENK concentration. All results were within the measurement of the assay, the lowest PENK concentration was 9 pmol/L. These results indicating the suitability of the used assay (assay sensitivity 5.5 pmol/L).

PENK and Prediction of Breast Cancer

We assessed the relationship between Pro-Enkephalin and breast cancer (Table 6). There was a strong relationship between Pro-Enkephalin and breast cancer in females. In a fully adjusted model each SD increase of Pro-Enkephalin was associated with a 28.6% risk reduction or each SD of decrease of Pro-Enkephalin (revPENK) was associated with a 40% increased risk of future breast cancer (table 5) and the top versus bottom quartile of Pro-Enkephalin identified a more than 3-fold difference in risk of breast cancer (see table 7 and FIG. 3).

TABLE 6

Variables in the Equation$^D$

|  | B | SE | Wald | df | Sig. | Exp(B) | 95.0% CI for Exp(B) | |
|---|---|---|---|---|---|---|---|---|
|  |  |  |  |  |  |  | Lower | Upper |
| AGE | .007 | .016 | .228 | 1 | .633 | 1.007 | .977 | 1.039 |
| SEX |  |  |  | 0$^a$ |  |  |  |  |
| BMI_B | .026 | .025 | 1.139 | 1 | .286 | 1.027 | .978 | 1.077 |
| DM_B | −.242 | .407 | .352 | 1 | .553 | .785 | .354 | 1.744 |
| HDL_B | .044 | .252 | .031 | 1 | .860 | 1.045 | .638 | 1.714 |
| LDL_B | −.001 | .090 | .000 | 1 | .988 | .999 | .837 | 1.191 |
| current_smoker | .330 | .195 | 2.886 | 1 | .089 | 1.392 | .950 | 2.037 |
| HER_CANCER_0 | .034 | .176 | .038 | 1 | .846 | 1.035 | .733 | 1.461 |
| LNINS | −.288 | .197 | 2.127 | 1 | .145 | .750 | .509 | 1.104 |
| ZscoreLNPENK_females_noCa | −.337 | .082 | 16.858 | 1 | .000 | .714 | .608 | .839 |

TABLE 7

BREAST CANCER

|  | HR per 1 SD | P-value | Quartile 4 | Quartile 3 | Quartile 2 | Quartile 1 | P for trend |
|---|---|---|---|---|---|---|---|
| Women (2140/135) | 1.40 (1.3-1.6) | <0.001 | 1.0 (ref) | 1.50 (0.81-2.1) | 2.7 (1.7-3.4) | 3.6 (2.7-4.9) | <0.001 |

Multivariate Cox proportional Hazards models for baseline Pro-Enkephalin versus incidence of breast cancer.

Figure 3:
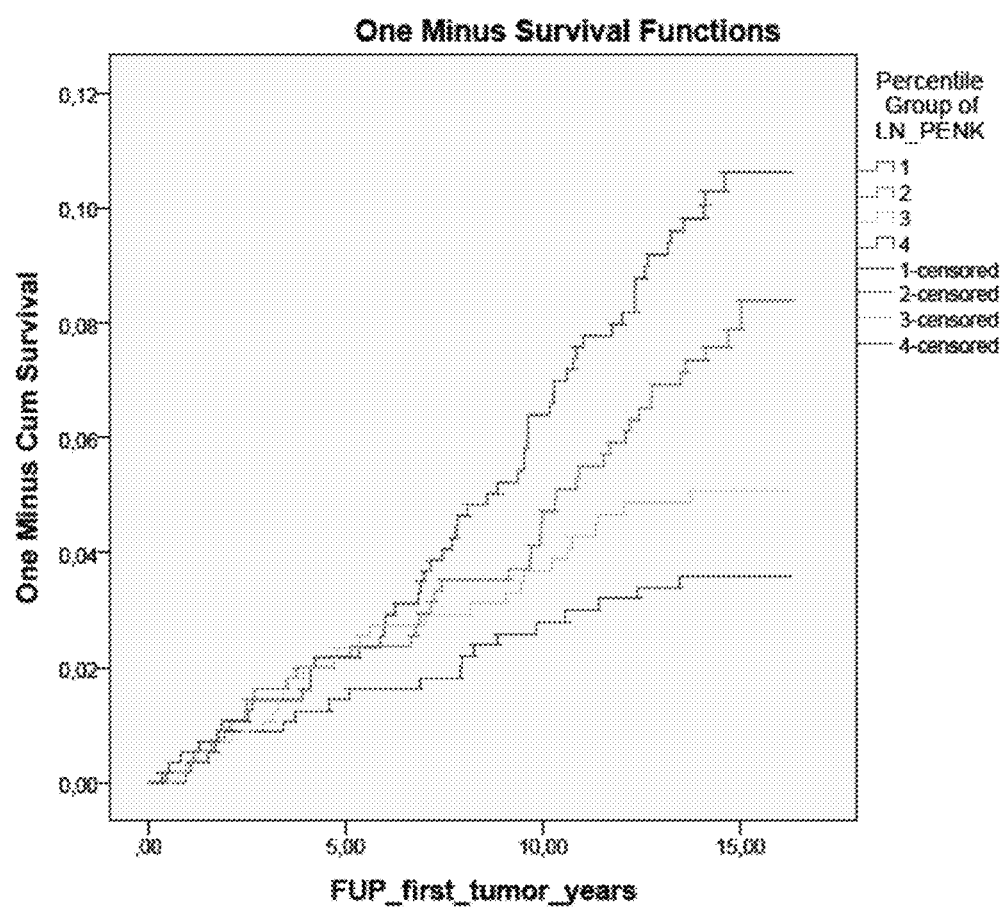

FIG. 3: Kaplan Meier graphs, illustrating the cumulative breast cancer diagnosis in women Quartile (Q) 1 (below 40.4 pmol/l) quartile 2 (40.4-47.1 pmol/l), quartile 3 (47.2-54.1 pmol/l), quartile 4 (above 54.1 pmol/l). Decreased PENK indicates a long term increased risk of breast cancer development. Since any women with cancer history at day of baseline (blood sampling) were excluded, Pro-Enkephalin is highly predictive for future breast cancer development. Overall, women from Q 1 have a 3.6 times higher risk to develop breast cancer than women from Q 4.

Combination Pro Enkephalin and Pro Neurotensin

Since increasing Pro-Neurotensin recently was shown to be highly predictive for breast cancer, we combined both biomarkers for breast cancer prediction.

EXAMPLES

Pro-Neurotensin Assay

Antibodies were generated as described above. The antibody for labelling (LA) was generated against P-NT 1-19 (H-CSDSEEEMKALEADFLTNMH (SEQ ID NO: 24)) and the solid phase antibody (SPA) was generated against peptide P-NT 44-62 (CNLNSPAEETGEVHEEELVA (SEQ ID NO: 25)).

Immunoassay for the Quantification of Human Pro-Neurotensin

The technology used was a sandwich coated tube luminescence immunoassay, based on Acridinium ester labelling. Labelled compound (tracer): 100 μg (100 μl) LA (1 mg/ml in PBS, pH 7.4, was mixed with 10 μl Acridinium NHS-ester (1 mg/ml in acetonitrile, InVent GmbH, Germany) (EP 0353971) and incubated for 20 min at room temperature. Labelled LA was purified by gel-filtration HPLC on Bio-Sil SEC 400-5 (Bio-Rad Laboratories, Inc., USA) The purified LA was diluted in (300 mmol/l potassiumphosphate, 100 mmol/l NaCl, 10 mmol/l Na-EDTA, 5 g/l bovine serum albumin, pH 7.0). The final concentration was approx. 800.000 relative light units (RLU) of labelled compound (approx. 20 ng labeled antibody) per 200 μl Acridiniumester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with SPA (1.5 μg SPA/0.3 ml 100 mmol/1 NaCl, 50 mmol/1 Tris/HCl, pH 7.8). After blocking with 5% bovine serum albumine, the tubes were washed with PBS, pH 7.4 and vacuum dried.

Calibration:

The assay was calibrated, using dilutions of Pro-Neurotensin containing human serum. A pool of human sera with high Pro-Neurotensin immunoreactivity (InVent Diagostika, Hennigsdorf, Germany) was diluted with horse serum (Biochrom AG, Deutschland) (assay standards).

The standards were calibrated by use of the human Pro-Neurotensin-calibrator (ICI-Diagnostics, Berlin, Germany). Alternatively, the assay may be calibrated by synthetic or recombinant P-NT 1-117 or fragments thereof (see also Ernst et al., 2006).

ProNT Immunoassay:

50 μl of sample (or calibrator) was pipetted into SPA coated tubes, after adding labeled LA (200 ul), the tubes were incubated for 16-22 h at 18-25° C. Unbound tracer was removed by washing 5 times (each 1 ml) with washing solution (20 mmol/l PBS, pH 7.4, 0.1% Triton X-100). Tube-bound LA was measured by using the Luminumeter LB 953. Results were calculated from the calibration curve.

Combined analysis of Pro-Enkephalin and PNT in the female population:

There was no significant correlation between Pro-Enkephalin and Pro-Neurotensin (p=0.56). In a combined model using both biomarkers, we found them both independent in breast cancer prediction.

In a fully adjusted model each SD increase of PNT was associated with a 49.9% risk increase of future breast cancer. Surprisingly, after adding PNT to the equation, PENK (SEQ ID NO: 1) was even stronger than without PNT and showed for each SD increase of Pro-Enkephalin a 30.8% risk reduction or each SD of decrease of Pro-Enkephalin (revPENK) was associated with a 44.5% increased risk of future breast cancer (table 8).

TABLE 8 combined analysis of PNT and PENK for breast cancer prediction.
Variables in the Equation

| | B | SE | Wald | df | Sig. | Exp(B) | 95.0% CI for Exp(B) Lower | Upper |
|---|---|---|---|---|---|---|---|---|
| AGE | −.003 | .019 | .020 | 1 | .888 | .997 | .960 | 1.036 |
| current_smoker0 | .434 | .204 | 4.505 | 1 | .034 | 1.543 | 1.034 | 2.304 |
| BMI_B | .001 | .027 | .001 | 1 | .979 | 1.001 | .948 | 1.056 |
| GFR_CG_BSAcorr | −.005 | .008 | .357 | 1 | .550 | .995 | .979 | 1.011 |
| hrt_curr | .730 | .201 | 13.146 | 1 | .000 | 2.075 | 1.399 | 3.079 |
| PNT | .405 | .091 | 19.731 | 1 | .000 | 1.499 | 1.254 | 1.793 |
| PENK | −.368 | .088 | 17.416 | 1 | .000 | .692 | .582 | .823 |

Highest vs. lowest quartile PNT indicated a 2.56 fold risk for breast cancer development and Pro Enkephalin on top of PNT lowest vs highest quartile (rev=reversed quartiles Q1=Q4, Q2=Q3, Q3=Q2, Q4=Q1)) an independent 3.6 fold risk (table 9).

Combining highest quartile of PNT and lowest Pro-Enkephalin quartile vs. lowest PNT- and highest Pro-Enkephalin quartile showed a combined risk of 6.17 (see FIG. 3).

Table 9: combined analysis of PNT and PENK for breast cancer prediction.

TABLE 9

Variables in the Equation

| | B | SE | Wald | df | Sig. | Exp(B) | 95.0% CI Lower |
|---|---|---|---|---|---|---|---|
| AGE | −.022 | .018 | 1.468 | 1 | .226 | .978 | .943 |
| current_smoker0 | .391 | .200 | 3.808 | 1 | .051 | 1.478 | .998 |
| hrt_curr | .652 | .195 | 11.145 | 1 | .001 | 1.920 | 1.309 |
| BMI_B | .012 | .025 | .247 | 1 | .619 | 1.012 | .964 |
| GFR_CG_BSAcorr | −.012 | .008 | 2.279 | 1 | .131 | .988 | .972 |
| NLN_PNT | | | 13.898 | 3 | .003 | | |
| NLN_PNT(1) | .353 | .301 | 1.378 | 1 | .241 | 1.424 | .789 |
| NLN_PNT(2) | .604 | .286 | 4.452 | 1 | .035 | 1.830 | 1.044 |
| NLN_PNT(3) | .942 | .269 | 12.260 | 1 | .000 | 2.566 | 1.514 |
| Q_PENK_rev | | | 23.361 | 3 | .000 | | |
| Q_PENK_rev(1) | .410 | .331 | 1.534 | 1 | .215 | 1.507 | .787 |
| Q_PENK_rev(2) | .979 | .305 | 10.299 | 1 | .001 | 2.663 | 1.464 |
| Q_PENK_rev(3) | 1.284 | .300 | 18.315 | 1 | .000 | 3.610 | 2.005 |

Figure 4:
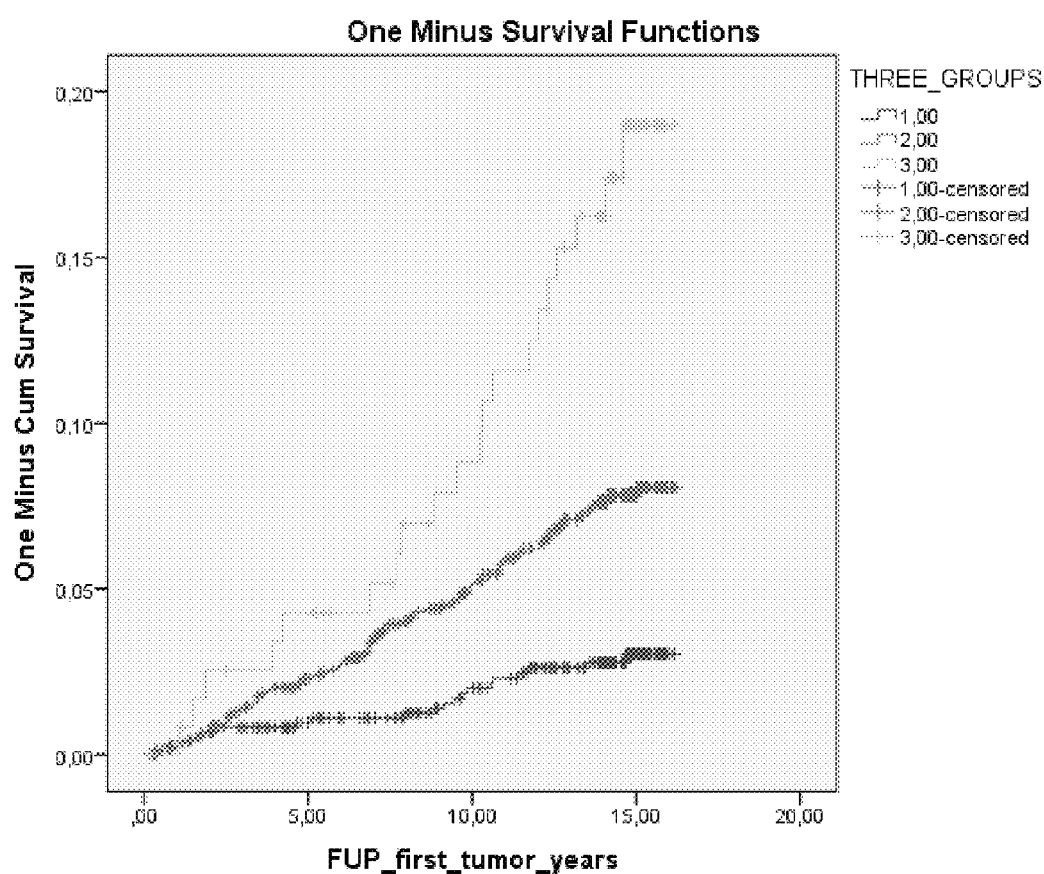

FIG. 4: Illustration example of combined analysis of Pro-Enkephalin for breast cancer prediction:

We combined the women with lowest Pro-Enkephalin (1$^{st}$) quartile and highest (4$^{th}$) Pro-Neurotensin quartile (group 3). Within that high risk group about 19.02% of women developed breast cancer within the following 15 years.

Group 2 is a combination of women with 3$^{rd}$ quartile of Pro-Neurotensin and 2$^{nd}$ quartile of Pro-Enkephalin plus 2$^{nd}$ quartile of Pro-Neurotensin and 3th quartile of Pro-Enkephalin. Within that medium risk group about 7.48% of women developed breast cancer within the following 15 years.

Group 1 is a combination of women with 1$^{st}$ quartile of Pro-Neurotensin and 4$^{th}$ quartile of Pro-Enkephalin. Within that low risk group about 3.08% of women developed breast cancer within the following 15 years. The Hazard risk between group 1 and group 3 is about 6.17.

Lung Cancer

Pro-Enkephalin also predicts lung cancer in females.

40 women developed lung cancer during the observation period. Pro-Enkephalin is not different in smoking and not smoking women (p=0.44). As expected, smoking is a strong risk prediction marker for lung cancer (p<0.0001). Surprisingly, although smoking is part of the equation, low Pro-Enkephalin indicated a 3.2 fold risk of developing lung cancer (table 10a and 10b).

Table 10 a and 10 b: PENK (SEQ ID NO. 1) in the prediction of lung cancer in females. The women were grouped in tertiles (see table 10 a) and then analyzed for lung cancer development (see table 10 b). rev=highest tertile (tertile 3), rev (1)=tertile 2 and rev(2)=lowest tertile (tertile 1).

TABLE 10 a

PENK [pmol/L]

Percentile Group of PENKpmolL

| | Median | Minimum | Maximum |
|---|---|---|---|
| 1 | 37,80000 | 9,000 | 42,800 |
| 2 | 47,20000 | 42,900 | 51,300 |
| 3 | 58,30000 | 51,400 | 518,100 |
| Total | 47,25000 | 9,000 | 518,100 |

TABLE 10 b

Variables in the Equation

|  | B | SE | Wald | df | Sig. | Exp(B) |
|---|---|---|---|---|---|---|
| AGE | .045 | .040 | 1.251 | 1 | .263 | 1.046 |
| current_smoker0 | 1.897 | .427 | 19.761 | 1 | .000 | 6.667 |
| BMI_B | −.034 | .063 | .287 | 1 | .592 | .967 |
| GFR_CG_BSAcorr | −.024 | .019 | 1.592 | 1 | .207 | .976 |
| T_PENK_females_rev |  |  | 6.698 | 2 | .035 |  |
| T_PENK_females_rev(1) | .208 | .580 | .128 | 1 | .721 | 1.231 |
| T_PENK_females_rev(2) | 1.168 | .511 | 5.220 | 1 | .022 | 3.214 |

FIGURE DESCRIPTION

FIG. 1: shows a typical Pro-Enkephalin dose/signal curve. Standard curve Pro-Enkephalin.

FIG. 2: frequency distribution of Pro-Enkephalin in the females population:

FIG. 3: Kaplan Meier graphs, illustrating the cumulative breast cancer diagnosis in women quartile (Q) 1 (below 40.4 pmol/l) quartile 2 (40.4-47.1 pmol/l), quartile 3 (47.2-54.1 pmol/l), quartile 4 (above 54.1 pmol/l). Decreased PENK indicates a long term increased risk of breast cancer development. Since any women with cancer history at day of baseline (blood sampling) were excluded, Pro-Enkephalin is highly predictive for future breast cancer development. Over all, women from Q 1 have a 3.6 times higher risk to develop breast cancer than women from Q 4.

FIG. 4: Illustration example of combined analysis of Pro-Enkephalin for breast cancer prediction:

The invention claimed is:

1. A method for predicting a risk of getting cancer in a female subject that does not suffer from cancer, wherein said cancer is breast cancer or lung cancer, said method comprising:

measuring the level of Pro-Enkephalin or fragments thereof of at least 5 amino acids in a sample of serum or plasma obtained from said female subject using an immunoassay that has antibodies or fragments of antibodies that bind to Pro-Enkephalin or said fragments thereof;

correlating said level of Pro-Enkephalin or fragments thereof with a risk of said subject for getting breast or lung cancer, wherein a reduced level is predictive for an enhanced risk of getting breast or lung cancer; and treating said subject with an anti-breast cancer or an anti-lung cancer treatment;

wherein a reduced level of Pro-Enkephalin or fragments thereof is a level below 100 pmol/l, and wherein said Pro-Enkephalin or fragment thereof is SEQ ID No. 1, SEQ ID No. 2, SEQ ID No. 5, SEQ ID No. 6, SEQ ID No. 8, SEQ ID No. 9, SEQ ID No. 10, or SEQ ID No. 11 and wherein the immunoassay comprises:

a) bringing said serum or plasma sample into contact with a solid phase comprising a bound first antibody or first antibody fragment that binds to Pro-Enkephalin or fragments thereof whereby Pro-Enkephalin or said fragments thereof within said sample react with said bound first antibody or antibody fragment to form a complex bound to said solid phase, b) contacting said solid phase with the bound complex with a second antibody or second antibody fragment, wherein said second antibody or second antibody fragment is labelled with a detectable label, and whereby the labelled second antibody or second antibody fragment binds to said complex, and c) measuring the level of Pro-Enkephalin or fragments thereof in said sample by measuring the amount of labelled second antibody or second antibody fragment bound to the complex on said solid phase.

2. The method according to claim 1, wherein said female subject has never had a history of diagnosis of cancer at the time said sample of serum or plasma is taken from said female subject.

3. The method according to claim 1, wherein said female subject has had a history of diagnosis of cancer and has been cured at the time said sample of serum or plasma is taken from said female subject and the risk of reoccurrence of getting breast cancer is determined or alternatively the reoccurrence of breast cancer is diagnosed.

4. The method according to claim 1, wherein at the time said sample of serum or plasma is taken from said female subject, said female subject has been diagnosed as having a cardiovascular disease or diabetes.

5. The method according to claim 1, further comprising determining at least one clinical parameter selected from age, presence of diabetes mellitus, and currently smoking.

6. The method according to claim 1, wherein said method is used to stratify female subjects into risk groups.

7. The method according to claim 1, wherein said cancer is breast cancer.

8. The method according to claim 1, wherein said correlating is performed by:

(a) comparing the level of Pro-Enkephalin or fragments thereof of at least 5 amino acids in said sample of serum or plasma obtained from said female subject with the median of the level of Pro-Enkephalin or fragments thereof of at least 5 amino acids an ensemble of pre-determined samples in a population of "healthy" or "apparently healthy" subjects, (b) comparing the level of Pro-Enkephalin or fragments thereof of at least 5 amino acids in said sample of serum or plasma obtained from said female subject with a quantile of the level of Pro-Enkephalin or fragments thereof of at least 5 amino acids an ensemble of pre-determined samples in a population of "healthy" or "apparently healthy" subjects, or (c) calculating the risk by Cox Proportional Hazards analysis or by Risk index calculations using the level of Pro-Enkephalin or fragments thereof of at least 5 amino acids in said sample of serum or plasma obtained from said female subject.

9. The method according to claim 1, wherein one of either (a) said bound first antibody or first antibody fragment, or (b) said labelled second antibody or second antibody fragment, binds to a peptide consisting of amino acid sequence 133-140 of Pro-Enkephalin, and the other of (a) said bound first antibody or first antibody fragment, and (b) said labelled second antibody or second antibody fragment, binds to a peptide consisting of amino acid sequence 152-159 of Pro-Enkephalin.

10. The method according to claim 1, wherein said method is performed more than once in order to monitor the risk of getting breast cancer in said female subject or in order to monitor the course of treatment for breast cancer.

11. The method according to claim 10, wherein monitoring is performed in order to evaluate the response of said female subject to preventive and/or therapeutic measures taken.

12. The method according to claim 1, further comprising measuring the level of Pro-Neurotensin 1-117 (SEQ ID No. 17) in a sample of serum or plasma obtained from said female subject using an immunoassay that has antibodies or fragments of antibodies that bind to Neurotensin 1-117 (SEQ ID No. 17); and correlating said level of Pro-Enkephalin or fragments thereof and said level of Pro-Neurotensin 1-117 (SEQ ID No. 17) with a risk for getting breast cancer or lung cancer, wherein a reduced level of Pro-Enkephalin is predictive for an enhanced risk of getting breast cancer or lung cancer, or alternatively diagnosing breast cancer or lung cancer wherein said reduced level of Pro-Enkephalin is correlated with the diagnosis of breast cancer or lung cancer and wherein an increased level of Pro-Neurotensin is predictive for an enhanced risk of getting breast cancer or lung cancer or alternatively diagnosing breast cancer or lung cancer wherein said increased level of Pro-Neurotensin is correlated with the diagnosis of breast cancer or lung cancer.

13. The method according to claim 12, wherein an increased level of Pro-Neurotensin or fragments thereof is a level above 78 pmol/l.

14. The method according to claim 12, wherein said measuring comprises measuring the level of MR-Pro-Enkephalin (SEQ ID No. 6) and measuring the level Pro-Neurotensin 1-117 (SEQ ID No. 17).

15. The method according to claim 12, wherein said cancer is breast cancer.

16. The method according to claim 12, wherein the measuring of the level of Pro-Neurotensin or fragment thereof comprises:
  a) bringing said sample of serum or plasma into contact with a solid phase comprising a bound third antibody or third antibody fragment that binds to Pro-Neurotensin or said fragment thereof whereby Pro-Neurotensin said fragment thereof within said sample reacts with said bound third antibody or third antibody fragment to form a complex bound to said solid phase,
  b) bringing said solid phase with the bound complex into contact with a fourth antibody or fourth antibody fragment, wherein said fourth antibody or fourth antibody fragment is labelled with a detectable label, and whereby the labelled fourth antibody or fourth antibody fragment binds to said complex, and
  c) measuring the level of Pro-Neurotensin or fragment thereof in said sample by measuring the amount of labelled fourth antibody or fourth antibody fragment bound to the complex on said solid phase.

17. The method according to claim 16, wherein
  one of either (a) said bound third antibody or third antibody fragment, or (b) said labelled fourth antibody or fourth antibody fragment, binds to a peptide consisting of amino acid sequence 1-19 of Pro-Neurotensin, and
  the other of (a) said bound third antibody or third antibody fragment, and (b) said labelled fourth antibody or fourth antibody fragment, binds to a peptide consisting of amino acid sequence 44-62 of Pro-Neurotensin.

18. The method according to claim 12, wherein
  one of either (a) said bound first antibody or first antibody fragment, or (b) said labelled second antibody or second antibody fragment, binds to a peptide consisting of amino acid sequence 133-140 of Pro-Enkephalin, and
  the other of (a) said bound first antibody or first antibody fragment, and (b) said labelled second antibody or second antibody fragment, binds to a peptide consisting of amino acid sequence 152-159 of Pro-Enkephalin.

19. The method according to claim 18, wherein the measuring of the level of Pro-Neurotensin or fragment thereof comprises:
  a) bringing said sample of serum or plasma into contact with a solid phase comprising a bound third antibody or third antibody fragment that binds to Pro-Neurotensin or said fragment thereof whereby Pro-Neurotensin said fragment thereof within said sample reacts with said bound third antibody or third antibody fragment to form a complex bound to said solid phase,
  b) bringing said solid phase with the bound complex into contact with a fourth antibody or fourth antibody fragment, wherein said fourth antibody or fourth antibody fragment is labelled with a detectable label, and whereby the labelled fourth antibody or fourth antibody fragment binds to said complex, and
  c) measuring the level of Pro-Neurotensin or fragment thereof in said sample by measuring the amount of labelled fourth antibody or fourth antibody fragment bound to the complex on said solid phase.

20. The method according to claim 19, wherein
  one of either (a) said bound third antibody or third antibody fragment, or (b) said labelled fourth antibody or fourth antibody fragment, binds to a peptide consisting of amino acid sequence 1-19 of Pro-Neurotensin, and
  the other of (a) said bound third antibody or third antibody fragment, and (b) said labelled fourth antibody or fourth antibody fragment, binds to a peptide consisting of amino acid sequence 44-62 of Pro-Neurotensin.

* * * * *

```
SEQUENCE LISTING

<160> NUMBER OF SEQ ID NOS: 25

<210> SEQ ID NO 1
<211> LENGTH: 243
<212> TYPE: PRT
<213> ORGANISM: Homo sapiens

<400> SEQUENCE: 1

Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
    50                  55                  60

Lys Pro Glu Glu Ser His Leu Leu Ala Lys Arg Tyr Gly Gly Phe Met
65                  70                  75                  80

Lys Arg Tyr Gly Gly Phe Met Lys Lys Met Asp Glu Leu Tyr Pro Met
                85                  90                  95

Glu Pro Glu Glu Glu Ala Asn Gly Ser Glu Ile Leu Ala Lys Arg Tyr
            100                 105                 110

Gly Gly Phe Met Lys Lys Asp Ala Glu Glu Asp Asp Ser Leu Ala Asn
        115                 120                 125

Ser Ser Asp Leu Leu Lys Glu Leu Leu Glu Thr Gly Asp Asn Arg Glu
    130                 135                 140

Arg Ser His His Gln Asp Gly Ser Asp Asn Glu Glu Val Ser Lys
145                 150                 155                 160

Arg Tyr Gly Gly Phe Met Arg Gly Leu Lys Arg Ser Pro Gln Leu Glu
                165                 170                 175

Asp Glu Ala Lys Glu Leu Gln Lys Arg Tyr Gly Gly Phe Met Arg Arg
            180                 185                 190

Val Gly Arg Pro Glu Trp Trp Met Asp Tyr Gln Lys Arg Tyr Gly Gly
        195                 200                 205

Phe Leu Lys Arg Phe Ala Glu Ala Leu Pro Ser Asp Glu Glu Gly Glu
    210                 215                 220

Ser Tyr Ser Lys Glu Val Pro Glu Met Glu Lys Arg Tyr Gly Gly Phe
225                 230                 235                 240

Met Arg Phe
```

<210> SEQ ID NO 2
<211> LENGTH: 73
<212> TYPE: PRT
<213> ORGANISM: Homo sapiens

<400> SEQUENCE: 2

Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
    50                  55                  60

Lys Pro Glu Glu Ser His Leu Leu Ala
65                  70

<210> SEQ ID NO 3
<211> LENGTH: 5
<212> TYPE: PRT
<213> ORGANISM: Homo sapiens

<400> SEQUENCE: 3

Tyr Gly Gly Phe Met
1               5

<210> SEQ ID NO 4
<211> LENGTH: 5
<212> TYPE: PRT
<213> ORGANISM: Homo sapiens

<400> SEQUENCE: 4

Tyr Gly Gly Phe Leu
1               5

<210> SEQ ID NO 5
<211> LENGTH: 20
<212> TYPE: PRT
<213> ORGANISM: Homo sapiens

<400> SEQUENCE: 5

Met Asp Glu Leu Tyr Pro Met Glu Pro Glu Glu Ala Asn Gly Ser
1               5                   10                  15

Glu Ile Leu Ala
            20

<210> SEQ ID NO 6
<211> LENGTH: 41
<212> TYPE: PRT
<213> ORGANISM: Homo sapiens

<400> SEQUENCE: 6

Asp Ala Glu Glu Asp Asp Ser Leu Ala Asn Ser Ser Asp Leu Leu Lys
1               5                   10                  15

Glu Leu Leu Glu Thr Gly Asp Asn Arg Glu Arg Ser His His Gln Asp
            20                  25                  30

Gly Ser Asp Asn Glu Glu Glu Val Ser
        35                  40

<210> SEQ ID NO 7
<211> LENGTH: 8

```
<212> TYPE: PRT
<213> ORGANISM: Homo sapiens

<400> SEQUENCE: 7

Tyr Gly Gly Phe Met Arg Gly Leu
1               5

<210> SEQ ID NO 8
<211> LENGTH: 12
<212> TYPE: PRT
<213> ORGANISM: Homo sapiens

<400> SEQUENCE: 8

Ser Pro Gln Leu Glu Asp Glu Ala Lys Glu Leu Gln
1               5                   10

<210> SEQ ID NO 9
<211> LENGTH: 11
<212> TYPE: PRT
<213> ORGANISM: Homo sapiens

<400> SEQUENCE: 9

Val Gly Arg Pro Glu Trp Trp Met Asp Tyr Gln
1               5                   10

<210> SEQ ID NO 10
<211> LENGTH: 22
<212> TYPE: PRT
<213> ORGANISM: Homo sapiens

<400> SEQUENCE: 10

Phe Ala Glu Ala Leu Pro Ser Asp Glu Gly Glu Ser Tyr Ser Lys
1               5                   10                  15

Glu Val Pro Glu Met Glu
            20

<210> SEQ ID NO 11
<211> LENGTH: 29
<212> TYPE: PRT
<213> ORGANISM: Homo sapiens

<400> SEQUENCE: 11

Phe Ala Glu Ala Leu Pro Ser Asp Glu Gly Glu Ser Tyr Ser Lys
1               5                   10                  15

Glu Val Pro Glu Met Glu Lys Arg Tyr Gly Gly Phe Met
            20                  25

<210> SEQ ID NO 12
<211> LENGTH: 7
<212> TYPE: PRT
<213> ORGANISM: Homo sapiens

<400> SEQUENCE: 12

Tyr Gly Gly Phe Met Arg Phe
1               5

<210> SEQ ID NO 13
<211> LENGTH: 147
<212> TYPE: PRT
<213> ORGANISM: Homo sapiens

<400> SEQUENCE: 13

Ser Asp Ser Glu Glu Glu Met Lys Ala Leu Glu Ala Asp Phe Leu Thr
1               5                   10                  15
```

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu Lys Arg Gln
        115                 120                 125

Leu Tyr Glu Asn Lys Pro Arg Arg Pro Tyr Ile Leu Lys Arg Asp Ser
    130                 135                 140

Tyr Tyr Tyr
145

<210> SEQ ID NO 14
<211> LENGTH: 125
<212> TYPE: PRT
<213> ORGANISM: Homo sapiens

<400> SEQUENCE: 14

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu
        115                 120                 125

<210> SEQ ID NO 15
<211> LENGTH: 6
<212> TYPE: PRT
<213> ORGANISM: Homo sapiens

<400> SEQUENCE: 15

Lys Ile Pro Tyr Ile Leu
1               5

<210> SEQ ID NO 16
<211> LENGTH: 13
<212> TYPE: PRT
<213> ORGANISM: Homo sapiens

<400> SEQUENCE: 16

```
Gln Leu Tyr Glu Asn Lys Pro Arg Arg Pro Tyr Ile Leu
1               5                   10
```

<210> SEQ ID NO 17
<211> LENGTH: 117
<212> TYPE: PRT
<213> ORGANISM: Homo sapiens

<400> SEQUENCE: 17

```
Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
                20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
                100                 105                 110

Lys Glu Glu Val Ile
        115
```

<210> SEQ ID NO 18
<211> LENGTH: 132
<212> TYPE: PRT
<213> ORGANISM: Homo sapiens

<400> SEQUENCE: 18

```
Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
                20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
                100                 105                 110

Lys Glu Glu Val Ile Lys Arg Lys Ile Pro Tyr Ile Leu Lys Arg Gln
        115                 120                 125

Leu Tyr Glu Asn
    130
```

<210> SEQ ID NO 19
<211> LENGTH: 21
<212> TYPE: PRT
<213> ORGANISM: Homo sapiens

<400> SEQUENCE: 19

```
Lys Ile Pro Tyr Ile Leu Lys Arg Gln Leu Tyr Glu Asn Lys Pro Arg
```

-continued

```
                1               5                  10                 15
Arg Pro Tyr Ile Leu
            20

<210> SEQ ID NO 20
<211> LENGTH: 28
<212> TYPE: PRT
<213> ORGANISM: Homo sapiens

<400> SEQUENCE: 20

Lys Ile Pro Tyr Ile Leu Lys Arg Gln Leu Tyr Glu Asn Lys Pro Arg
1               5                   10                  15

Arg Pro Tyr Ile Leu Lys Arg Asp Ser Tyr Tyr Tyr
            20                  25

<210> SEQ ID NO 21
<211> LENGTH: 20
<212> TYPE: PRT
<213> ORGANISM: Homo sapiens

<400> SEQUENCE: 21

Gln Leu Tyr Glu Asn Lys Pro Arg Arg Pro Tyr Ile Leu Lys Arg Asp
1               5                   10                  15

Ser Tyr Tyr Tyr
            20

<210> SEQ ID NO 22
<211> LENGTH: 8
<212> TYPE: PRT
<213> ORGANISM: Homo sapiens

<400> SEQUENCE: 22

Leu Lys Glu Leu Leu Glu Thr Gly
1               5

<210> SEQ ID NO 23
<211> LENGTH: 8
<212> TYPE: PRT
<213> ORGANISM: Homo sapiens

<400> SEQUENCE: 23

Ser Asp Asn Glu Glu Glu Val Ser
1               5

<210> SEQ ID NO 24
<211> LENGTH: 20
<212> TYPE: PRT
<213> ORGANISM: Homo sapiens

<400> SEQUENCE: 24

Cys Ser Asp Ser Glu Glu Glu Met Lys Ala Leu Glu Ala Asp Phe Leu
1               5                   10                  15

Thr Asn Met His
            20

<210> SEQ ID NO 25
<211> LENGTH: 20
<212> TYPE: PRT
<213> ORGANISM: Homo sapiens

<400> SEQUENCE: 25

Cys Asn Leu Asn Ser Pro Ala Glu Glu Thr Gly Glu Val His Glu Glu
1               5                   10                  15
```

```
Glu Leu Val Ala
           20
```